(12) United States Patent
Moussavi et al.

(10) Patent No.: US 8,412,596 B2
(45) Date of Patent: Apr. 2, 2013

(54) BIOLOGICAL REAGENT CATALOG

(75) Inventors: Mahcameh Moussavi, Lenexa, KS (US); Kevin Matthew Power, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 87 days.

(21) Appl. No.: 12/650,823

(22) Filed: Dec. 31, 2009

(65) Prior Publication Data

US 2011/0161207 A1    Jun. 30, 2011

(51) Int. Cl.
*G06Q 10/00* (2012.01)
*G06K 9/46* (2006.01)
(52) U.S. Cl. .......................................... 705/28; 382/190
(58) Field of Classification Search ...................... 705/28
See application file for complete search history.

(56) References Cited

U.S. PATENT DOCUMENTS

| 2002/0059030 A1* | 5/2002 | Otworth et al. ................. 702/19 |
| 2006/0045348 A1* | 3/2006 | Kiros et al. .................... 382/190 |
| 2007/0203747 A1* | 8/2007 | Baharloo et al. .................. 705/2 |

* cited by examiner

*Primary Examiner* — Garcia Ade
(74) *Attorney, Agent, or Firm* — Shook Hardy & Bacon L.L.P.

(57) ABSTRACT

Embodiments relate to providing one or more recommended biological reagents in response to receiving a biological reagent order. An exemplary embodiment includes identifying biological reagents based on a biological reagent order that has been received. Characteristic data of the identified biological reagents may then be evaluated to identify a characteristic conflict among the identified biological reagents. Similarly, inventory data of the identified biological reagents may then be evaluated to identify an inventory conflict among the identified biological reagents. If a conflict, either characteristic or inventory, is identified, a recommendation for an alternative biological reagent may be provided that is free from conflict. Additionally, historical use data may be maintained and referenced to aid in identifying a biological reagent as either a potential biological reagent based on a suspected biological condition or as a substitute biological reagent.

20 Claims, 11 Drawing Sheets

| PROBE | MANUFACTURER | LOT NUMBER | EXP DATE | FLUOROPHORE (COLOR) | PROBE LOCATION | TYPE | REGIONS OF INTEREST | |
|---|---|---|---|---|---|---|---|---|
| CEP 3 | VYSIS | 198475 | 1/10 | RED | 3P11.1-Q11.1 | ALPHA SATELLITE DNA | 400.3P11.1 | ... |
| | | | | | | | 400.3P11.1 | |
| CEP 7 | VYSIS | 475802 | 2/11 | GREEN | 7P11.1-Q11.1 | ALPHA SATELLITE DNA | 400.7P11.1 | ... |
| | | | | | | | 400.7P11.1 | |
| LSI P16 | VYSIS | 234648 | 3/10 | GOLD | 9P21 | BAND | (GDNA),MLLT3 | ... |
| | | | | | | | 400.9P21 | |
| P53 | MPBIO | 34587034 | 9/10 | GREEN | 17P13 | GENE | (GDNA),TP53 | ... |
| | | | | | | | 400.17P13 | |
| C-MYC | MPBIO | 45879890 | 8/9 | AQUA | 6Q21 | GENE | (GDNA),MYC | ... |
| | | | | | | | 400.8Q24 | |
| ATM | MPBIO | 43972301 | 12/9 | YELLOW | 11Q23 | GENE | (GDNA),ATM | ... |
| | | | | | | | 400.11Q22 | |
| T(9;22) | MPBIO | 58849210 | 1/10 | RED | 9Q34/22Q11 | TRANSLOCATION | T(9;22)(Q34;Q11) | ... |
| | | | | | | | (GDNA),BCR | |
| | | | | | | | (GDNA),ABL | |

BIOLOGICAL REAGENT CATALOG

BACKGROUND

Generally, a laboratory responsible for fulfilling a biological reagent order would rely on trained laboratory technicians that are able to identify genetic regions of interest for a suspected biological condition associated with the order. The laboratory technician may then reference a database or journal to identify a biological reagent, such as a fluorescence in situ hybridization probe, that may be appropriate for identifying the genetic region of interest. Unfortunately, this traditional approach is prone to error and inefficiencies. For example, inventory data and quality control information for biological reagents may not be evaluated or may require additional laboratory technician time to investigate.

SUMMARY

Embodiments of the present invention relate to systems, methods, and computer storage media for providing one or more recommended biological reagents in response to receiving a biological reagent order. An exemplary embodiment includes identifying biological reagents based on a biological reagent order that has been received. Characteristic data of the identified biological reagents may then be evaluated to identify a characteristic conflict among the identified biological reagents. In an additional embodiment of the present invention, inventory data of the identified biological reagents is then evaluated to identify an inventory conflict among the identified biological reagents. If a conflict, either characteristic or inventory, is identified, a recommendation for an alternative biological reagent is provided that is free from conflict. Similarly, historical use data may be maintained and referenced to aid in identifying a biological reagent as either a potential biological reagent based on a suspected biological condition or as a substitute biological reagent. Further, in additional embodiments, quality control information is maintained and utilized to provide reporting capabilities regarding biological reagents.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

Illustrative embodiments of the present invention are described in detail below with reference to the attached drawing figures, which are incorporated by reference herein and wherein:

FIG. 5 depicts a data structure table illustrating exemplary characteristic and inventory data for a plurality of probes in accordance with an embodiment of the present invention;

DETAILED DESCRIPTION

Figure 1:
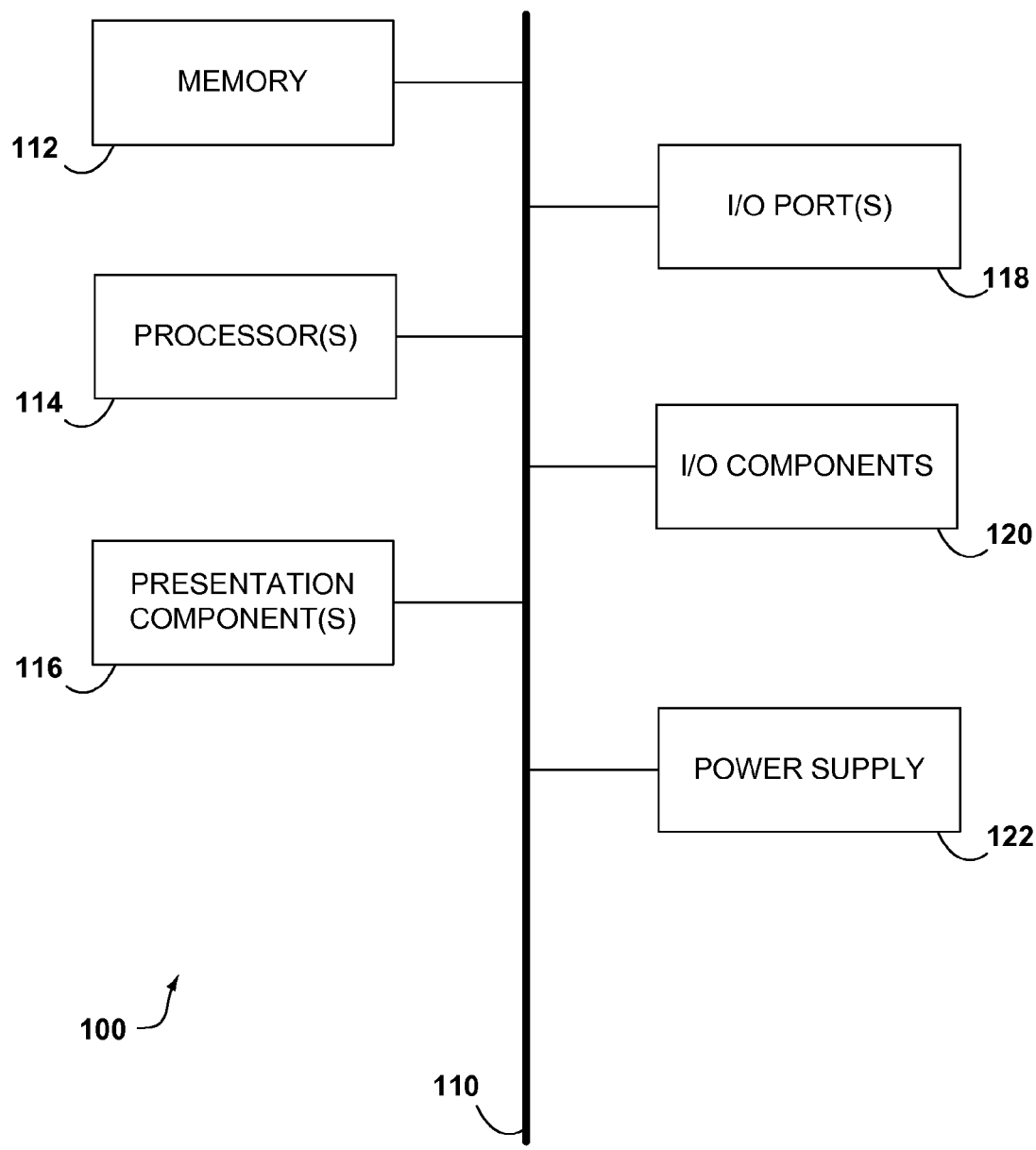
FIG. 1 depicts an exemplary computing device suitable for implementing embodiments of the present invention.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the present invention relate to systems, methods and computer storage media for providing one or more recommended biological reagents in response to receiving a biological reagent order. An exemplary embodiment includes identifying one or more biological reagents based on the received biological reagent order. Characteristic data of the one or more identified biological reagents is evaluated to identify a characteristic conflict among the identified biological reagents. In an additional embodiment of the present invention, inventory data of the one or more identified biological reagents is evaluated to identify an inventory conflict among the identified biological reagents. If a conflict, either characteristic or inventory, is identified, a recommendation for an alternative biological reagent is provided that is free from conflict.

Accordingly, in one aspect, the present invention provides computer storage media having computer-executable instructions embodied thereon, that when executed by a computing system having a processor and memory, cause the computing system to perform a method for providing recommended biological reagents in response to a request. The method includes receiving a request for one or more biological reagents, wherein the request is comprised of a suspected biological condition and/or one or more specific biological reagents. The method also includes identifying the one or more biological reagents capable of fulfilling the request. The method also includes evaluating characteristic data of the one or more biological reagents to identify a characteristic conflict with at least one characteristic of the one or more biological reagents. The method additionally includes evaluating inventory data of the one or more biological reagents to identify an inventory conflict with one or more inventory controls of the one or more biological reagents. The method also includes providing, in response to the request, a response including one or more recommended biological reagents, wherein the one or more recommended biological reagents are provided based, at least in part, on the evaluation of the characteristic data and the evaluation of the inventory data.

In another aspect, the present invention provides a method providing recommended biological reagents in response to a biological reagent order. The method includes receiving, at a computing device having a processor and memory, the order, wherein the order includes a first biological reagent and a second biological reagent. The method also includes identifying, with the computing device, a characteristic conflict between the first specified biological reagent and the second biological reagent. The method also includes identifying a third biological reagent as a substitute for the second biological reagent, wherein the first biological reagent and the third biological reagent are free of the characteristic conflict. The method also includes providing a response to the order that identifies at least the first biological reagent and the third biological reagent.

A third aspect of the present invention provides computer storage media having computer-executable instructions embodied thereon, that when executed by a computing system having a processor and memory, cause the computing system to perform a method for providing one or more biological reagents for a diagnostic test. The method includes receiving an order for one or more biological reagents to perform a diagnostic test functional to identify a biological condition, wherein the order includes an identifier of the biological condition. The method also includes accessing a data store to retrieve information, wherein the information includes characteristic data, inventory data, and historical data of one or more biological reagents. The method also includes identifying the one or more biological reagents based on the information, wherein a predetermined conflict threshold is achieved by the one or more biological reagents. Additionally, the method includes communicating an identifier for each of the one or more biological reagents.

Having briefly described an overview of embodiments of the present invention, an exemplary operating environment suitable for implementing embodiments hereof is described below.

Referring to the drawings in general, and initially to FIG. 1 in particular, an exemplary operating environment suitable for implementing embodiments of the present invention is shown and designated generally as computing device 100. Computing device 100 is but one example of a suitable computing environment and is not intended to suggest any limitation as to the scope of use or functionality of the invention. Neither should the computing environment 100 be interpreted as having any dependency or requirement relating to any one or combination of modules/components illustrated.

Embodiments may be described in the general context of computer code or machine-useable instructions, including computer-executable instructions such as program modules, being executed by a computer or other machine, such as a personal data assistant or other handheld device. Generally, program modules including routines, programs, objects, modules, data structures, and the like, refer to code that performs particular tasks or implements particular abstract data types. Embodiments may be practiced in a variety of system configurations, including hand-held devices, consumer electronics, general-purpose computers, specialty computing devices, etc. Embodiments may also be practiced in distributed computing environments where tasks are performed by remote-processing devices that are linked through a communications network.

With continued reference to FIG. 1, computing device 100 includes a bus 110 that directly or indirectly couples the following devices: memory 112, one or more processors 114, one or more presentation modules 116, input/output (I/O) ports 118, I/O modules 120, and an illustrative power supply 122. Bus 110 represents what may be one or more busses (such as an address bus, data bus, or combination thereof). Although the various blocks of FIG. 1 are shown with lines for the sake of clarity, in reality, delineating various modules is not so clear, and metaphorically, the lines would more accurately be grey and fuzzy. For example, one may consider a presentation module such as a display device to be an I/O module. Also, processors have memory. The inventors hereof recognize that such is the nature of the art, and reiterate that the diagram of FIG. 1 is merely illustrative of an exemplary computing device that can be used in connection with one or more embodiments. Distinction is not made between such categories as "workstation," "server," "laptop," "hand-held device," etc., as all are contemplated within the scope of FIG. 1 and reference to "computer" or "computing device."

Computing device 100 typically includes a variety of computer-readable media. By way of example, and not limitation, computer-readable media may comprise Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices; or any other medium that can be used to encode desired information and be accessed by computing device 100.

Memory 112 includes computer-storage media in the form of volatile and/or nonvolatile memory. The memory may be removable, non-removable, or a combination thereof. Exemplary hardware devices include solid-state memory, hard drives, optical-disc drives, etc. Computing device 100 includes one or more processors that read data from various entities such as memory 112 or I/O modules 120. Presentation module(s) 116 present data indications to a user or other device. Exemplary presentation modules include a display device, speaker, printing module, vibrating module, and the like. I/O ports 118 allow computing device 100 to be logically coupled to other devices including I/O modules 120, some of which may be built in. Illustrative modules include a microphone, joystick, game pad, satellite dish, scanner, printer, wireless device, and the like.

Figure 2:
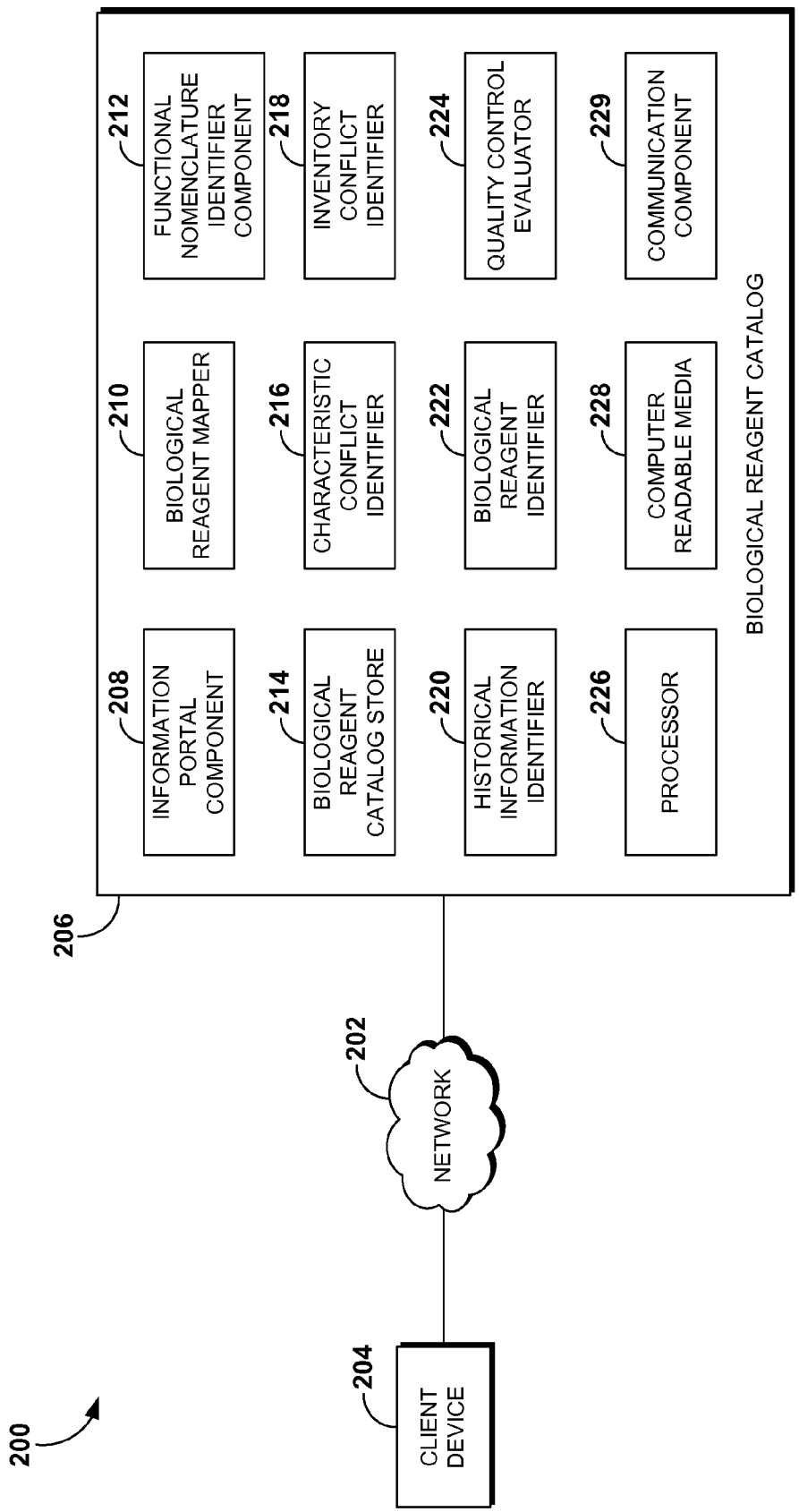
FIG. 2 depicts an environment for an exemplary system in which embodiments of the present invention may be employed.

With reference to FIG. 2, a block diagram is provided illustrating an exemplary system 200 in which embodiments of the present invention may be employed. It should be understood that this and other arrangements described herein are set forth only as examples. Other arrangements and elements (e.g., machines, interfaces, functions, components, and grouping of components, etc.) can be used in addition to or instead of those shown, and some elements may be omitted altogether. Further many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the system 200 may include a client device 204, a biological reagent catalog 206, and a data storage (not shown). Each of the components in FIG. 2 may be, or coupled with, any type of computing device, such as computing device 100 described with reference to FIG. 1, for example. The various components may communicate with each other via a network 202, which may include, without limitation, local networks, one or more local area networks (LANs) and/or wide area networks (WANs). Such networking environments are commonplace in offices, enterprise-wide computer networks, intranets, and the Internet. Therefore, it is contemplated that the biological reagent catalog 206 may be implemented as a local service, as a distributed service (i.e., cloud based), or as some combination of the local and distributed services such that certain functionality is maintained locally while other functionality is distributed. It should be understood that any number of client devices 204, servers, computing devices, networks, data stores, and biological reagent catalogs 206 may be employed within the system 200 while still in the scope of the present invention. Additionally, other component not shown may also be included within the system 200.

Accordingly, any number of components may be employed to achieve the desired functionality within the scope of embodiments of the present invention. Although the various components of FIG. 2 are shown with lines for the sake of clarity, in reality, delineating various components is not so clear, and metaphorically, the lines would more accurately be grey or fuzzy. Further, although some components of FIG. 2 are depicted as single blocks, the depictions are exemplary in nature and in number and are not to be construed as limiting.

The client device 204, as previously discussed may be implemented as a computing device. For example, a physician, a healthcare provider (e.g., nurses, care assistants, technicians, lab technicians, pharmacists), and/or scientists may utilize a handheld computing device to enter information for electronic medical records, to enter pharmaceutical prescriptions, to enter laboratory orders, or the like. In yet another exemplary embodiment, the client device 204 is a work station at which a biological reagent order is entered by a healthcare provider or related entity. The lab order, in an exemplary embodiment, is ordered at the client device 204 to be reviewed, at least in part, by a medical technology solution such as PATHNET HELIX offered by Cerner Corporation of Kansas City, Mo.

The biological reagent catalog 206 is a computing device functional to review biological reagent orders. Examples of biological reagent review includes, but is not limited to, identifying a characteristic conflict, identifying an inventory conflict, identify a historical conflict, or the like. A biological reagent is a substance added to a system in order to cause or identify a reaction in biological material. An exemplary biological reagent is a fluorescence in situ hybridization (FISH) probe used to detect and/or localize the presence or absence of specific DNA sequences on chromosomes as part of a cytogenetic technique. Therefore, in an exemplary embodiment, the biological reagent catalog 206 is functional to review orders for one or more FISH probes when used as part of a cytogenetic analysis technique.

The biological reagent catalog 206 includes a number of devices and components. While specific components and devices are illustrated and discussed hereinafter, it is understood that additional or fewer components may be employed as part of the biological reagent catalog 206 in various embodiments of the present invention. As illustrated, the biological reagent catalog 206 includes an information portal component 208, a biological reagent mapper 210, a functional nomenclature identifier component 212, a biological reagent catalog store 214, a characteristic conflict identifier 216, an inventory conflict identifier 218, a historical information identifier 220, a biological reagent identifier 222, a quality control evaluator 224, a processor 226, computer readable media 228, and a communication component 229.

Initially, the biological reagent catalog 206 includes the processor 226 and the computer readable media 228. Each may be utilized in whole or in part by any or all of the various components and devices of the biological reagent catalog. For example, the characteristic conflict identifier 216, in an exemplary embodiment, utilizes both the processor 226 and the computer readable media 228 to identify one or more characteristic conflicts between biological reagents. Similarly, the communication component 229, which is functional to facilitate communication among one or more components and among one or more computing device(s), may be utilized by the characteristic conflict identifier 216 to communicate a recommendation for a biological reagent or a notification of a conflict to the client device 204.

The information portal component 208 is functional to receive data related to biological reagents. In an exemplary embodiment a healthcare provider, a manufacturer, or provider of a biological reagents may input information into the biological reagent catalog by way of the information portal component 208. For example, characteristic data, inventory data, and historical data, all of which will be discussed in greater detail at FIG. 3, may be input through the information portal component 208. In an exemplary embodiment, the information portal component 208 provides a portal, such as a form, data entry service, or the like where information may be input individually or in batch for use in reviewing biological reagent requests/orders by the biological reagent catalog 206.

The biological reagent mapper 210 and the function nomenclature identifier component 212, in an exemplary embodiment, facilitate maintaining a relationship between subjective trade names for each of the biological reagents and a functional nomenclature that is more objective. An exemplary functional nomenclature is the CLINICAL BIOINFORMATICS ONTOLOGY ("CBO") available from the Cerner Corporation of Kansas City, Mo., which is a structured vocabulary to describe genetic information. Therefore, while a particular laboratory or manufacturer may refer to a particular biological reagent by a trade name that is not universally distinguishable, the functional nomenclature identifier component 212 is able to review information of that biological reagent and create/generate a functional identifier that is universal. For example, a FISH probe may have a manufacturer's assigned name that is not descriptive of the regions of interest or even a related fluorophore (i.e., color) for that FISH probe, but the functional nomenclature identifier component 212 is able to take that information and generate an identifier that is functionally descriptive.

In turn, the biological reagent mapper 210 creates a relationship map between a biological reagent's trade name and a functional identifier created by the functional nomenclature identifier component 212. The relationship created by the biological reagent mapper 210 allows for various information sources to be utilized when reviewing biological reagent orders. For example, several laboratories may share historical data to provide a greater sample size, but a universal identifier for functionally equivalent biological reagents is useful to identify and associate related information. Therefore, while orders within a particular laboratory may include subjective trade names, the mapping to a universal functional identifier allows for the various trade-named biological reagents to be associated.

The biological reagent catalog store is a data store functional to store information related to biological reagents and the biological reagent catalog 206. For example, a structured storage service may be implemented in one or more embodiments to maintain information, such as characteristic data, inventory data, and historical data. The biological reagent catalog store 214 serves as a data store for that information. In an additional exemplary embodiment, the biological reagent catalog store 214 includes functionality to control, maintain, and monitor information useable by the biological reagent catalog 206. As a data store, the biological reagent catalog store 214 includes dedicated or universal computer readable media, such as the computer readable media 228.

The characteristic conflict identifier 216 is functional to identify a characteristic conflict between two or more biological reagents. For example, characteristic data may include regions of interest that a FISH probe is functional to identify as well as a color that the FISH probe will fluoresce.

A biological reagent order may include two specified FISH probes. In an exemplary embodiment, the characteristic conflict identifier 216 evaluates characteristic data associated with each of the specified FISH probes. The characteristic information, in this example, indicates that while each of the FISH probes highlights different locations in the biological matter, both FISH probes identify their respective locations with a red fluoresce. Therefore, the characteristic conflict identifier 216 identifies a characteristic conflict of the two FISH probes as a conflict between the fluorophore of the FISH probes contained in the biological reagent order. As a result, in an exemplary embodiment, the characteristic conflict identifier 216, is also functional to identify a substituted biological reagent that has a similar diagnostic functionality as one of the biological reagents, but free from a characteristic conflict. For example, the characteristic conflict identifier 216 is able to identify a FISH probe that is able to identify a similar or the same region of interest as one of the biological reagents contained in the original order, but the substitute FISH probe fluoresces a different color. A first biological reagent has a similar diagnostic functionality of a second biological reagent when an intended diagnostic result of the first biological reagent is satisfied by the second biological reagent.

A biological reagent order is free from characteristic conflict when the one or more biological reagents of the order do not exceed a predetermined conflict threshold. For example, a predetermined conflict threshold may be established so that no conflicts are allowed between characteristics of the biological reagents. In yet an additional exemplary embodiment, a predetermined conflict threshold may be established so that only conflicts of a certain type are avoided. For example, characteristic conflicts of a region of interests may not exceed the conflict threshold, but a conflict with fluorophore (or other diagnostic indicators) characteristic information would exceed the predefined conflict threshold.

The inventory conflict identifier 218 is functional to identify a conflict with inventory information of one or more biological reagents. An inventory conflict results when one or more inventory metrics or information exceeds a predetermined inventory conflict threshold. For example, as will be discussed more with respect to FIG. 3, inventory data may include expiration information. In an exemplary embodiment, an inventory threshold may be established so that when an expiration date exceeds the current date, the inventory conflict threshold has been exceeded. Therefore, biological reagents that have expired are identified by the inventory conflict identifier 218. In an exemplary embodiment, the inventory conflict identifier 218 is also functional to recommend a substitute biological reagent when a conflict is identified. For example, the inventory conflict identifier 218 may locate and recommend a functionally similar biological reagent to a biological reagent that was identified as having an inventory conflict. A functional nomenclature for each of the biological reagents may be employed to aid in identifying a functionally similar biological reagent.

An additional exemplary embodiment of the present invention includes identifying an inventory conflict when quality control metrics exceed a predefined inventory conflict threshold. For example, the biological reagent catalog 206 may track and store various quality control statistics that are associated with the inventory data of each biological reagent. When one or more of the quality control statistics (e.g., standard deviation, lot number tracking or monitoring) exceed a predefined inventory conflict threshold, a recommendation for a substitute biological reagent may be offered by the inventory conflict identifier 218. Further, in an additional exemplary embodiment, a notice may be presented bringing attention to the inventory conflict. In yet an additional exemplary embodiment, the notice may be preemptive to serve as a warning that one or more inventory conflicts may arise in a number of days, uses, or iterations. For example, the inventory data, in an exemplary embodiment, indicates the quantity of an ordered biological reagent is running low relative to a predefined conflict threshold, therefore, the inventory conflict identifier 218 may provide a notice of the pending conflict.

The historical information identifier 220 is functional to identify historical information related to a biological reagent to recommend a substitute or available biological reagent. For example, in some instances a biological reagent order does not include specific biological reagents but instead a suspected biological condition that may be identifiable by performing an evaluation with one or more biological reagents. In this example where the order does not include specified biological reagents, the historical information identifier 220 is able to identify one or more biological reagents, based on previous rules and/or orders, that are able to satisfy the biological reagent order. For example, a physician may suspect a certain type of leukemia for a patient and therefore the physician may provide an order for a cytogenetic analysis utilizing unspecified FISH probes capable of preliminarily identifying the suspected leukemia. Based on historical information that associates a FISH probe 'A' and a FISH probe 'B' as being used in concert to identify the suspected biological condition of leukemia, the historical information identifier 220 may propose the use of the FISH probe 'A' and the FISH probe 'B' in response to the physician's order.

The historical information identifier 220 is also functional to identify preferred substitute biological reagents. For example, when a characteristic or inventory conflict is identified for a biological reagent (or combination of biological reagents) and one or more substitute biological reagents are available, the historical information identifier 220 is able to identify one or more substitutes based on historical information (e.g., previously utilized substitutes, replacements, comparables).

The historical information identifier 220, in an exemplary embodiment, utilizes historical information that is particular to: a requester, a clinic, an organization, a geographic location, a patient, a profession, or from a combined pool from any of the above. The historical information is used to determine a suggested or substitute biological reagent received from one or several of the above-referenced entities. Therefore, while the historical data may be very specialized to a particular requester (e.g., physician), it may draw on the experience of a greater group such as a whole organization (e.g., group of hospitals). Additionally, the historical information may be anonymous or otherwise blind to maintain information privacy.

The biological reagent identifier 222 is functional to identify a biological reagent. For example, when an ordered biological reagent is found to have a conflict, a substitute biological reagent may be necessary. The biological reagent identifier 222, in an exemplary embodiment, is functional to identify a substitute biological reagent. In an exemplary embodiment, the biological reagent identifier 222 provides the substitute biological reagent to the characteristic conflict identifier 216, the inventory conflict identifier 218, the historical information identifier 220, or other components of the biological reagent catalog.

An additional exemplary embodiment utilizes the biological reagent identifier 222 to identify one or more biological reagents for a biological reagent order that does not include specified biological reagent, but instead includes a suspected biological condition. In this example, the biological reagent identifier 222 may evaluate characteristic information, inventory information, and/or historical information when identifying one or more biological reagents capable of fulfilling the biological reagent order.

The quality control evaluator 224 is functional to evaluate and report quality control information to the biological reagent catalog 206 and a user of the client device 204. In an exemplary embodiment, the inventory data and historical data, either alone or in combination, maintain information that is valuable for identifying quality control concerns related to biological reagents. For example, a statistical analysis may be performed by accessing a data store containing diagnostic results associated with the biological reagents obtained from biological reagent orders processed through the biological reagent catalog 206. The results may then be analyzed to identify if one or more biological reagents are providing or causing results that would be considered a statistical outlier. An exemplary situation includes a FISH probe 'A' that is known, from information in a historical information data store, to average a count of 10,000 units across a typical sample of results; however, the quality control evaluator 224 may review results associated with the FISH probe 'A' from a certain lot or manufacturer and determine that the count is averaging 20,000 units. In this example, the quality control evaluator 224 may cause a notification to be provided to a user of the client device 204 at the time of detection or at some later point, such as the next time the FISH probe 'A' is a recommended or ordered biological reagent. The quality control evaluator 224 functions, in one embodiment, automatically so that a direct input is not required by a user. The automatic functionality of the quality control evaluator 224 therefore "runs in the background" evaluating a predefined set of quality control metrics that may be customized or generic, depending on the implementation. For example, a first lab may customize the quality control metrics based on the first lab's control standards. This is contrary to a second lab that follows an industry standard for quality control metrics. The second lab may therefore rely on default type metrics that coincide with an industry standard quality control evaluation technique.

In an additional exemplary embodiment, the quality control evaluator 224 functions in an active manner. For example, a user may request a quality control evaluation to be performed at a specified time, for specified biological reagents, over a specified period. Further, the active evaluation may be implemented automatically in association with receiving a biological reagent order or providing a recommendation for a biological reagent order. In this example, when a FISH probe 'A' is included in a biological reagent order, the quality control evaluator 224 may be instructed, by a user or a computing application executed on a computing device, to evaluate one or more metrics of the FISH probe 'A' for quality control purposes.

As previously discussed, a data store may be associated with the biological reagent catalog 206 in an exemplary embodiment. A data store is functional to store data that is used by or in conjunction with one or more elements/components of the biological reagent catalog 206. For example, the characteristic identifier 216, the inventory conflict identifier 218, and the historical information identifier 220, among other components, may store data, such as tables, utilized for identifying a conflict among biological reagents. It is understood that the storage (not shown in FIG. 2) may be integrated with, or coupled to by way of the network 202, the biological reagent catalog 206.

Figure 3:
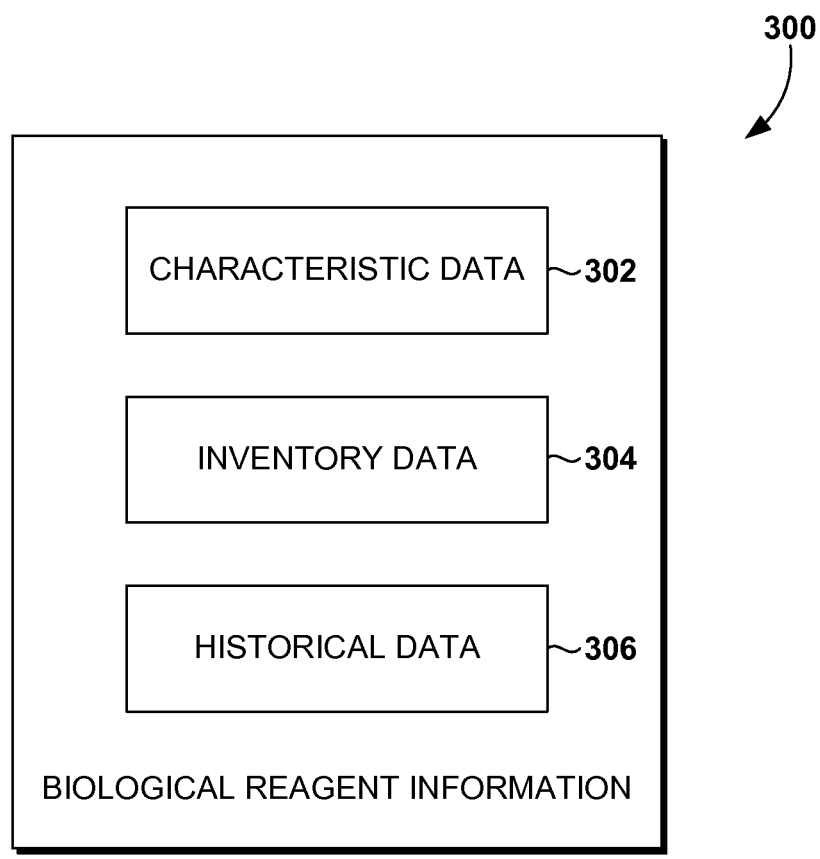
FIG. 3 depicts a block diagram illustrating biological reagent information in accordance with embodiments of the present invention.

With reference to FIG. 3, a block diagram illustrating biological reagent information 300 in accordance with embodiments of the present invention. The biological reagent information 300 includes, but is not limited to, characteristic data 302, inventory data 304, and historical data 306. In an exemplary embodiment, biological reagent information 300 includes information that is useable for performing the functionality previously discussed with respect to the biological reagent catalog 206. For example, identification of a conflict, characteristic, or inventory may be performed based on biological reagent information 300. An additional example includes identifying a biological reagent, such as a recommended biological reagent based on a suspected biological condition or a suspected biological reagent conflict in an order, wherein the recommendation may be performed based on biological reagent information 300.

The characteristic data 302 is information on characteristics and traits of a biological reagent. As will be discussed in more detail hereinafter at FIG. 5, a biological reagent typically has information that defines characteristics of the biological reagent. For example, a FISH probe, in an exemplary embodiment, has characteristics such as regions of interest, a probe location, a type, and a fluorophore. In this example a FISH probe 'A' may fluoresce red when viewed. Therefore, the characteristic data 302 will include information related to FISH probe 'A' that indicates that the color of fluoresce is red for the FISH probe 'A.' This characteristic data will be utilized, in an exemplary embodiment, to identify a characteristic conflict.

The inventory data 304 is information on inventory of a biological reagent. As will also be discussed in more detail hereinafter at FIG. 5, a biological reagent typically has information that defines one or more inventory control aspects of the biological reagent. For example, inventory data may include, but not be limited to, probe name, manufacturer, lot number, expiration data, functional ontology identifier, quantity remaining, quantity used, date of requests, date of entry into the system, and the like. In an exemplary embodiment, the inventory data 304 is utilized by the biological reagent catalog 206 of FIG. 2 to realize an inventory conflict. For example, an inventory conflict includes identifying a biological reagent has an expiration date that fails to exceed a threshold, such as the current date. As a result of this example, the inventory data 304 is used to provide a notification or warning as to the expiration date of a biological reagent.

The historical data 306 is information on a biological reagent and/or biological reagent orders that is/are used to provide a recommendation and to identify a conflict. For example, a healthcare provider provides a biological reagent order that only includes a suspected condition without specifying one or more biological reagents. In addition to additional information, the biological reagent catalog 206 of FIG. 2 will evaluate the historical data 306 to identify the one or more biological reagents that have been ordered or recommended previously for the suspected condition included in the original biological reagent order. In this example, the historical data 306 allows the system to become more intelligent, by learning, from previous operations, recommendations, and results. Historical data 306, in an additional exemplary embodiment, is also used to provide a recommendation to overcome conflicts. For example, two biological reagents may be available to overcome an identified conflict, the historical data 306 may be queried to narrow the recommendation to a previously or not previously used biological reagent. Further, instead of limiting the recommended biological reagents, the historical data 306 may be relied upon to rank the potentially recommended biological reagents for easier presentation and eventual selection by a healthcare provider or the like.

Biological reagent information 300 may include information particular to biological reagents accessible or useable at a specified location, or the biological reagent information 300 may include a larger pool of biological reagents and historical data. For example, a lab may desire to only rely on biological reagent information 300 from within its own system to prevent tainting the information with outside influences. In the alternative, a laboratory may allow characteristic data 302 and inventory data 304 (or any other combination of data) to be pulled from a larger pool, such as a cloud-based environment that allows manufacturers of biological reagents to provide character data and inventory data updates (e.g., known quality control issues, updated expiration, updated region of interest). In yet another exemplary embodiment, the biological reagent information 300 includes data from a large pool of sources that are aggregated and maintained by a third party for use as a provided service or as a subscription-type service. It is contemplated that any combination of data and sources may be implemented in embodiments of the present invention.

Figure 4:
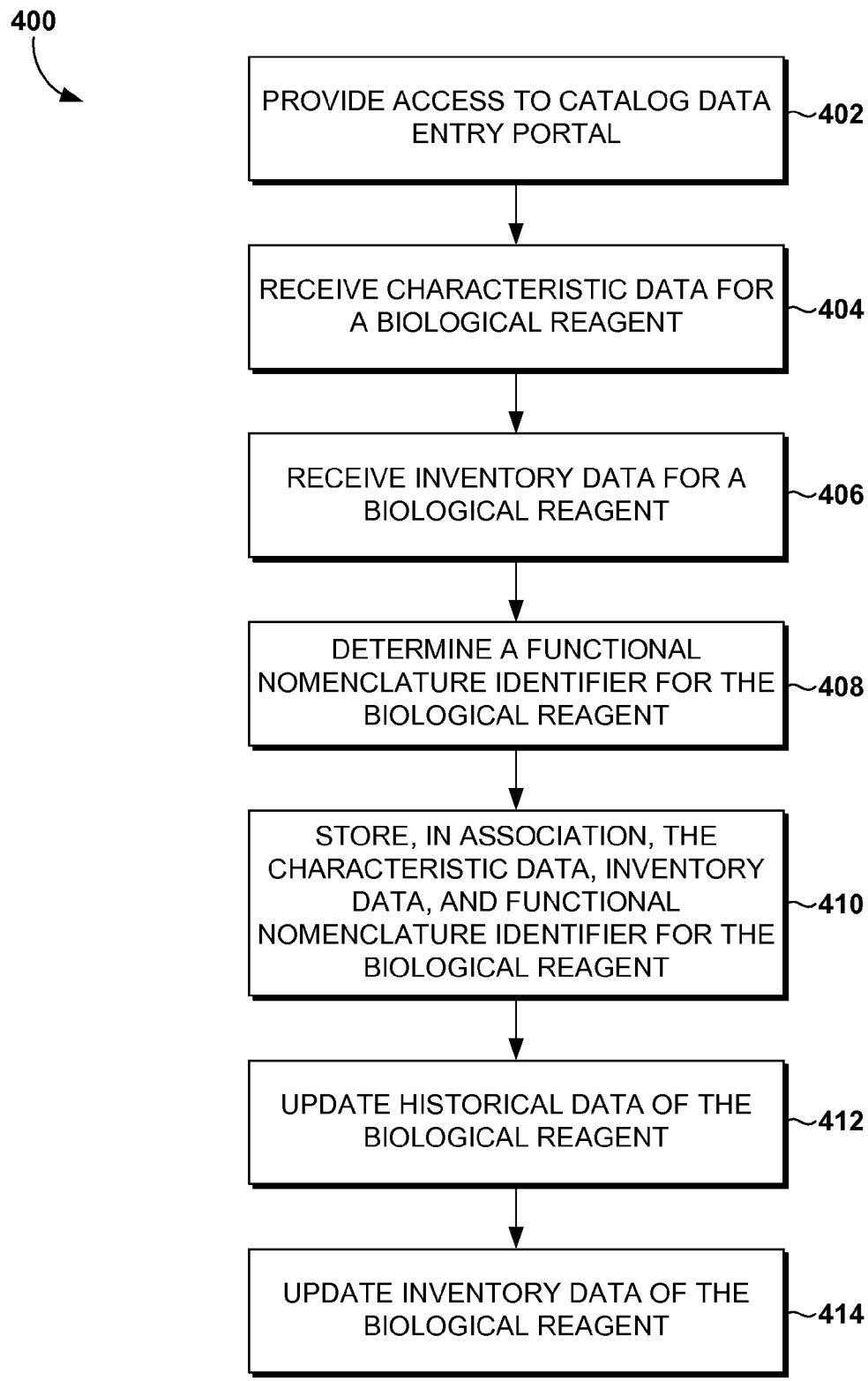
FIG. 4 depicts a flow diagram of a method to manage biological reagent information useable by a biological reagent catalog, in accordance with an embodiment of the present invention.

With reference to FIG. 4, that depicts a flow diagram of a method 400 to manage biological reagent information useable by a biological reagent catalog in accordance with an embodiment of the present invention. It is understood that the method 400 and other methods described herein may be implemented by a computing device having a processor and memory to transform information used as an input to a transformative result, such as data in a different useable form or format than the provided input.

At a step 402, access to a catalog data entry portal (e.g., a catalog data entry form) is provided. A data entry portal is a service or way to enter information, such as biological reagent information 300 of FIG. 3, related to one or more biological reagents into a system, such as the biological reagent catalog 206 of FIG. 2. An exemplary entry portal is an Internet-based form with a plurality of fields that a user may enter information into that will populate a data store, such as a database. Additional exemplary catalog data entry portals include file receiving portals. For example, data may be formatted in a recognized style to allow a file including the data to be ported to a system for conversion or deciphering into a format useable by the system. Examples include formatting data as a comma separated value (CSV) format, as Extensible Markup language (XML), or the like. Access to a catalog data entry portal is provided by allowing a user of computing device to submit or upload information, such as an XML file, to be received by a system. Therefore, providing access to catalog data entry portal may include allowing data to be entered that is related to one or more biological reagents. The data includes characteristic data, inventory data, and historical data. Additional data may include predefined threshold data, quality control standards and level data, and other forms of information and data useable by the biological reagent catalog 206 of FIG. 2.

In an exemplary embodiment, a Hypertext Markup Language (HTML) compatible page is provided that allows for the direct entry of information or provides a way to upload or otherwise access/retrieve a file containing information. Therefore, a user may access an Internet style browser and navigate to a particular page that allows entering of information. The biological reagent catalog provides the page as a catalog data entry portal in this exemplary embodiment.

At a step 404, characteristic data for a biological reagent is received. Characteristic data, as previously discussed, includes information that defines one or more characteristics of the biological reagent. For example, a region of interest and a luminance color may be characteristic data of a FISH probe. It is understood that different biological reagents may include different characteristic data. In an exemplary embodiment, the characteristic data is received through the catalog data entry portal to which access was provided. In an additional exemplary embodiment, at least part of the received characteristic data is received from a third party, such as an information provider or a manufacturer of the biological reagent. It is understood that a user, utilizing a computing device, may enter characteristic data.

At a step 406, inventory data for a biological reagent is received. As also previously discussed, inventory data may include information such as lot number, expiration date, as well as quantity information. The inventory data may be provided, at least in part, through a third party, such as an information provider or a manufacturer of the biological reagent. Additionally, it is understood that the inventory data may also be received from an automated process, such as an automated inventory control program that is responsible for maintaining an inventory of products, such as biological reagents.

It is contemplated that characteristic data and inventory data may be received in combination or as separate information. Additionally, it is contemplated that "receiving" includes the concept of pulling information from additional sources. For example, a user may enter a biological reagent identifier in a catalog data entry portal; the system may then use that biological reagent identifier to locate additional data, such as characteristic and inventory data (as well as other data) associated with that biological reagent. Therefore, a combination of user input and "pulled" data may be received.

At a step 408, a functional nomenclature identifier for the biological reagent is determined. A functional nomenclature identifier, as previously discussed, is an identifier that allows a biological reagent to be identified by characteristics or traits. An example of such a nomenclature is CBO, which has been previously discussed. In an exemplary embodiment, a trade name, such as a manufacturer derived name, for a biological reagent is received. A functional nomenclature identifier is then determined based on a previous mapping between the trade name and the functional nomenclature identifier. A mapping may be created locally from previous entries of a similar trade name biological reagent or the mapping may be provided, by way of a network, from a third party. It is contemplated that the functional nomenclature identifier is determined from a remote service offered by a third party. In an additional embodiment, characteristic data is reviewed by the system, such as the biological reagent catalog 206 of FIG. 2, to determine a functional nomenclature identifier for the biological reagent. A determination of a functional nomenclature identifier, in an exemplary embodiment, is performed utilizing one or more predefined rules. An example of creating a functional nomenclature is described in U.S. patent application Ser. No. 11/028,262 filed on Jan. 3, 2005, and titled "Computerized System And Method For Creating And Maintaining An Ontology For Genomics Concepts," which is herein incorporated by reference in its entirety.

At a step 410, the characteristic data, inventory data, and functional nomenclature identifier for the biological reagent are all stored in association. The association may be maintained by a data store so that access to one or more of the portions of information allows for the associated information to be queried. In an exemplary embodiment, a structured data store is utilized to maintain the association among the various data, such as the unique functional nomenclature identifier, the characteristic data, and the inventory data relevant to the underlying biological reagent. The storing may be done in one or more computer readable media accessible by a computing device having a processor and memory. In an exemplary embodiment, the computing device and the computer readable media are specialized to perform the task of maintaining, storing, and/or retrieving the data.

At a step 412, historical data for the biological reagent is updated. Historical data, as previously discussed with respect to FIG. 3, is information that includes trending and previous utilization information. For example, relationships among various biological agents contained on a common order or associated with a suspected condition may be maintained as historical data. The historical data may be utilized for identifying a recommended biological reagent or evaluating quality control data.

Historical data may be updated at each order, at each recognized fulfillment of an order, at specified times, or at user request. The historical data that is updated may also be updated based on unique preferences set by a user or a default update schedule and policy may be relied upon. It is contemplated that a combination of both update types may be implemented for the variety of information.

At a step 414, inventory data of the biological reagent is updated. Inventory data may include a quantity of biological reagents remaining. This quantity may be based on an anticipated usage from the biological orders provided or the quantity may also be based on confirmed biological orders that are fulfilled. A biological order is fulfilled when biological reagents have been dispensed from inventory for use in a diagnostic test. For example, a biological reagent order that includes two FISH probes is received by the biological reagent catalog, but in this example, the biological reagent order is not fulfilled until the FISH probes or recommended alternatives are provided in response to the original order.

Turning to FIG. 5, a table 500 depicting exemplary characteristic and inventory data for a plurality of FISH probes in accordance with an embodiment of the present invention. It is understood that the table 500 is merely exemplary and not limiting to the scope of the present invention. The table 500 includes a number of columns 502-516. Each column of the table 500 includes information that is relevant, in an exemplary embodiment, to functionality of a biological reagent catalog. For example, the table 500 may include various characteristic data, inventory data, and/or historical data for one or more biological reagents.

For example, the table 500 includes a column 502 that includes a listing of probe names. The probe names indicated in column 502 may be either a trade name or a functional nomenclature assigned the probe populating a particular row of table 500. Additionally, it is understood that the column 502 may be comprised of both trade names and functional nomenclature, such as that derived with the CBO. Column 504 includes a listing of manufacturers. The manufacturers may include commercial entities as well as local entities, such as a lab operating the biological reagent catalog associated with the table 500. Column 506 includes a lot number for each of the biological reagents. As previously discussed, the lot number may be used as part of inventory data.

The column 508 includes expiration dates for each of the biological reagents. An expiration date may be used as a threshold value when determining if there is an inventory conflict. For example, if a particular biological reagent "CEP 3" is associated with an expiration of January 2010, then a biological reagent order that includes CEP 3 may be evaluated to identify if the date of the order or issuance of the biological reagent is on or after the January 2010 date. Additionally, an inventory conflict may be established to identity a threshold that is above or below (e.g., after or before) a particular value. For example, an inventory conflict related to expiration (or any other date-based value) may have a time value added to or subtracted from it to provide a greater level of confidence. In this example, a predetermined value, such a 1 day, 1 week, 10 days, 2 weeks, 1 month, 6 weeks, etc., may be used so that an inventory conflict is raised before an actual expiration date indicated in the table 500.

The table 500 includes the column 510. Column 510 indicates a fluorophore or color that a particular biological reagent fluoresces when utilized in a diagnostic analysis. In general, the column 510 includes characteristic data. Therefore, depending on the biological reagents maintained within the table 500, the characteristic data may include different values or information. In an exemplary embodiment, a characteristic conflict is identified when a characteristic, such as those indicated in column 510, results in confusing or inaccurate diagnostic results because of an ambiguity caused by a particular characteristic. For example, when two biological reagents are used as part of a common diagnostic run, if the color in which each of the biological reagents fluoresces is similar, a characteristic conflict is identified. In an exemplary embodiment, one or more predefined rules are established for identifying characteristic conflicts. For example, a mapping between characteristics that may cause a characteristic conflict may be maintained by the biological reagent catalog. In this example, color combinations that typically cause confusion, such as identical colors or even similar colors, may be mapped to one another. When characteristics are mapped to one another in a characteristic conflict mapping, a conflict is represented. For example, a red fluoresce may be mapped to a pink fluoresce characteristic as causing a characteristic conflict because the two colors are too close to one another causing a potential ambiguity in diagnostic results. It is understood that the characteristic conflict mapping may be changed or updated at any point to reflect patient, health-care provider, laboratory, etc., specific characteristic conflicts that are acceptable or not acceptable.

The column 512 indicates a probe location. For example, in cytogenetics a band in which a biological reagent (e.g., probe) is associated may be identified. Identifying the location to which the probe is adapted to identify therefore allows a correct biological reagent to be selected for a particular diagnostic test. In addition to identifying a correct biological reagent, the probe location information may also be utilized when the biological reagent catalog is selecting one or more biological reagents for a biological reagent order that does not contain specified biological reagents or as a substitute biological reagent when a conflict exists or is identified. For example, a biological reagent that is identified as having a conflict, characteristic or inventory, may be substituted with a suggested biological reagent that is selected, at least in part, by identifying a probe location of one of the conflicted biological reagents. Once the probe location of a conflicted biological reagent is identified, the table 500 may be scanned for one or more biological reagents that have a probe location that at least covers the same or similar probe location of the conflicted biological reagent. In alternative embodiments, as previously discussed, a substitute biological reagent may be identified based on other information, such as historical information, predefined substitute listings, user preference, and the like.

The column 514 includes information related to a type of biological reagent identified at each row of table 500. For example, a biological reagent type may include a descriptive identifier of how a particular probe is traditionally utilized. A type designation may also be directed to a level of detail or type of identification that may be accomplished with the probe. For example, a probe named in column 502, "T(9:22)", has an associated type of "Translocation." The type, such as "Translocation", in some examples, is redundant to the probe name which may already signify that the probe is functional for identifying a translocation, but in other examples, the type identifier allows for the probes to be classified, sorted, and arranged for purposes of fulfilling the various responsibilities of a biological reagent catalog.

The column 516 includes regions of interest associated with each of the biological reagents included within table 500. Regions of interest may identify a particular location within biological matter, such as chromosome bands and regions, which a probe is effective to identify. Similar to a probe location, regions of interest may be utilized to identify one or more substitute biological reagents when a conflict exists. In an exemplary embodiment, the regions of interest information is redundant, at least in part, to the information included within the probe location. The regions of interest column 516, when utilized as part of an information portal, includes an elliptical indication allowing for a user to input additional information related to the particular probe. It is understood that the elliptical indication depicted within the column 516 may also be included within any and all columns of table 500 in an exemplary embodiment.

The table 500 illustrates an exemplary information portal for a user to enter information related to each of the biological reagents maintained by a biological reagent catalog. It is understood that the particular columns previously discussed and illustrated are exemplary and aid in the discussion surrounding the table 500. But, it is contemplated that additional columns including additional information are included with table 500. Similarly, it is contemplated that fewer or different columns of information are included with table 500. Additionally, it is contemplated that some, none, or all, of the biological reagents maintained within the table 500 have associated information for each of the columns. Therefore, not all types of information (i.e., columns) for a particular biological reagent are populated with information. As a result, the table 500 is functional to maintain a wide variety of biological reagents having a variety of associated biological reagent information useable by a biological reagent catalog, such as the biological reagent catalog 206 of FIG. 2.

Figure 6:
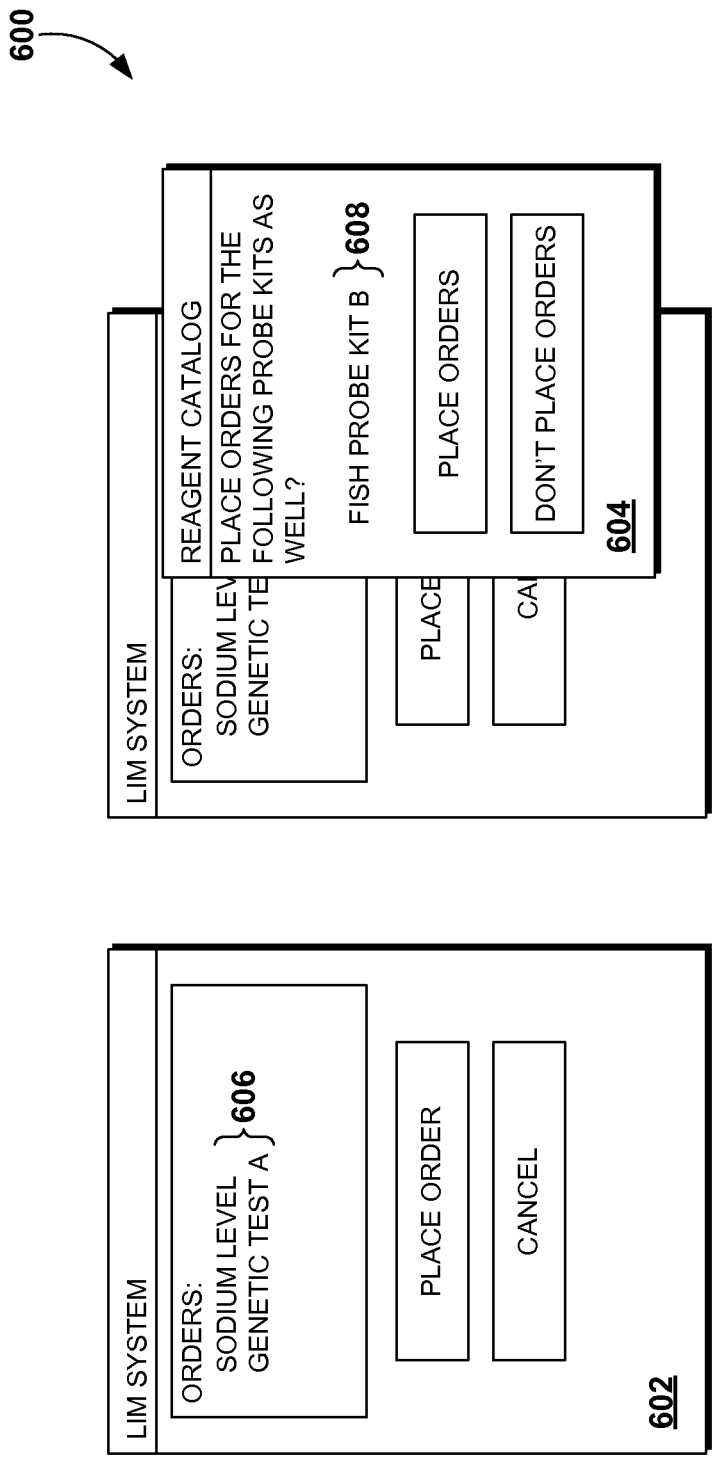
FIG. 6 illustrates a progression of Graphical User Interfaces (GUI) providing a suggested biological reagent based on a biological reagent order that does not include specified biological reagents in accordance with an embodiment of the present invention.

Turning to FIG. 6, that illustrates a progression of Graphical User Interfaces (GUI) 600 providing a suggested biological reagent based on a biological reagent order that does not include specified biological reagents in accordance with an embodiment of the present invention. The progression GUI 600 includes a first GUI 602, which is then followed by a second GUI 604 that includes an additional window notification. It is understood that the first GUI 602 and the second GUI 604 are merely exemplary and are not limiting as to all embodiments of the present invention but instead provide an exemplary embodiment.

The first GUI 602 includes several features of a biological order 606. The features may be a suspected (or known) biological condition, a suspected (or known) effective test regime identifier, and/or a suspected (or known) symptom. For example, the first GUI 602 includes the biological order 606 that includes a sodium level and a genetic test A. In this example, a specified biological reagent is not included with the order, but instead other information that may be used to identify a suspected biological reagent is included. Based on the information provided within the biological order 606, a biological reagent catalog may provide a suggested biological reagent(s) that is effective to complete the biological order 606.

Continuing with this example, the progression of GUI 600 then provides the second GUI 604, which includes an additional windowing space that includes a suggested biological reagent based on the order 606. In this example, the suggested biological reagent 608 indicates a particular FISH probe kit B, which may contain several biological reagents.

In practice, a user (e.g., healthcare provider, laboratory technician) enters an order (or received an order and reviews the order) at a biological reagent catalog as depicted at the first GUI 602. A user may then use an input device, such as a touch screen, mouse, or the like to provide an input, such as a button selection, to indicate the order should be placed. Upon receipt of the biological reagent order, the biological reagent catalog identifies that a specified biological reagent is not included or is needed in order to satisfy the received biological reagent order. As a result, the biological reagent order catalog identifies a biological reagent for presentation at the second GUI 604. The progression of GUI 600 therefore displays the second GUI 604 with the suggested biological reagents. In an exemplary embodiment, the biological reagent catalog identifies and cures conflicts associated with the suggested biological reagent 608 prior to presentation within the second GUI 604. The user, once presented with the second GUI, may then determine if the suggested biological reagent(s) fulfills the intent of the biological order 606. The user may then provide a confirmation input, such as selection of a GUI button, or the like to facilitate the actual ordering of the biological reagent.

It is understood that any combination, structure, or format may be implemented to provide one or more GUIs to a user or other in order to accomplish the objectives identified herein of a biological reagent catalog. For example, it is contemplated that additional options may be presented to the user based on the biological reagents maintained by the biological reagent catalog. Additionally, it is contemplated that additional information, such as inventory, characteristic, and/or historical information, is provided, or offered to be provided, along with the suggested biological reagents 608. Further, in an additional exemplary embodiment, the second GUI 604 is not utilized, but instead a biological reagent is ordered without user intervention. As a result, it is contemplated that any and all combinations of various GUI options may be implemented to facilitate the functionality of various embodiments of the present invention as discussed herein. It is understood that the first GUI 602 and the second GUI 604, in an exemplary embodiment, are displayed contemporaneously to one another. However, in an additional exemplary embodiment, the first GUI 602 and the second GUI 604 are presented serially to one another. Further, it is understood that the concepts conveyed by the first GUI 602 and the second GUI 604 may be presented in a manner that varies from that which is depicted in the exemplary FIG. 6.

Figure 7:
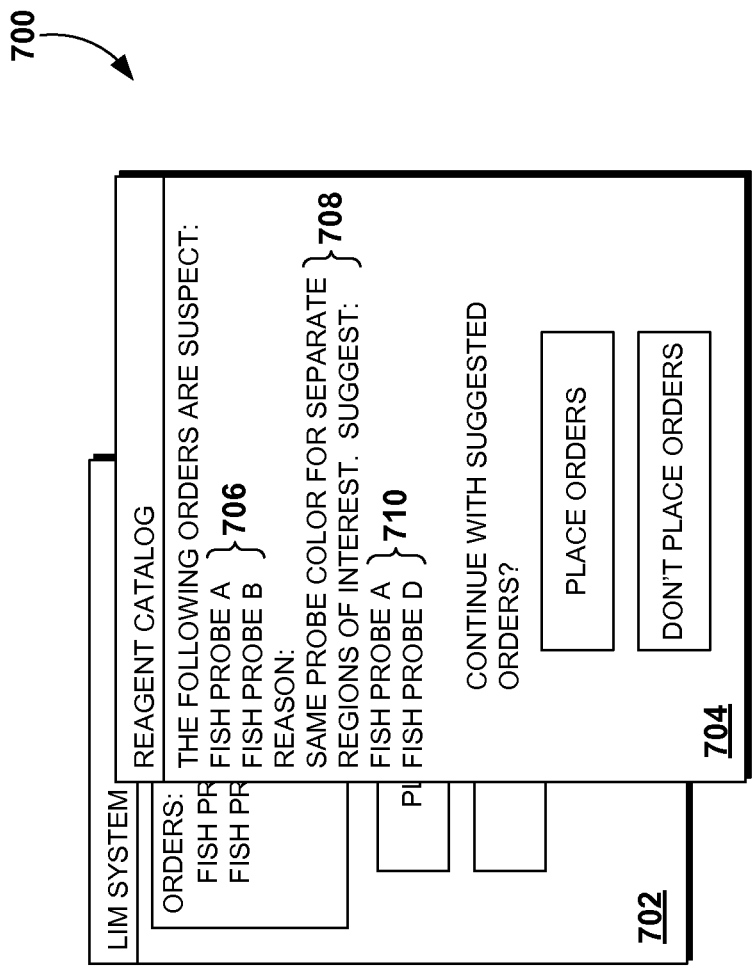
FIG. 7 depicts another exemplary GUI progression in accordance with embodiments of the present invention.

Turning to FIG. 7, that depicts another exemplary GUI progression 700 in accordance with embodiments of the present invention. The GUI progression 700 includes a first GUI 702 that depicts an entered (or received) biological reagent order. The GUI progression 700 also includes a second GUI 704. The second GUI 704 is presented in response to the biological reagent catalog identifying a conflict, such as a characteristic conflict or an inventory conflict. For example, an original biological reagent order presented in the first GUI 702 includes specified biological reagents of a FISH probe A and a FISH probe B. However, the biological reagent catalog identified a conflict, in this example a characteristic conflict. Therefore, the second GUI 704 identifies biological reagents suspected of the conflict 706. The second GUI additionally provides information related to the suspected conflict 708. In this example, the suspected characteristic conflict is based on similar probe color for different regions of interest. The second GUI 704 also includes one or more suggested biological reagents that avoid a conflict (and/or the identified conflict) 710. In this example, the second GUI 704 presents two biological reagents, a FISH probe 'A' and a FISH probe 'D'.

As previously discussed with respect to FIG. 6, it is contemplated that additional elements or different elements may be implemented with one or more of the GUIs illustrated herein. As such, it is understood that the GUIs as illustrated are exemplary in nature and not limiting to all embodiments of the present invention. As such, it is contemplated that information related to characteristic, inventory, history, conflicts, or the like may or may not be included with any or none of the illustrated or previously discussed GUIs. Further, it is understood that the concepts discussed herein are not limited to presentation by way of a GUI, but instead may also be presented by way of alternative methods.

Figure 8:
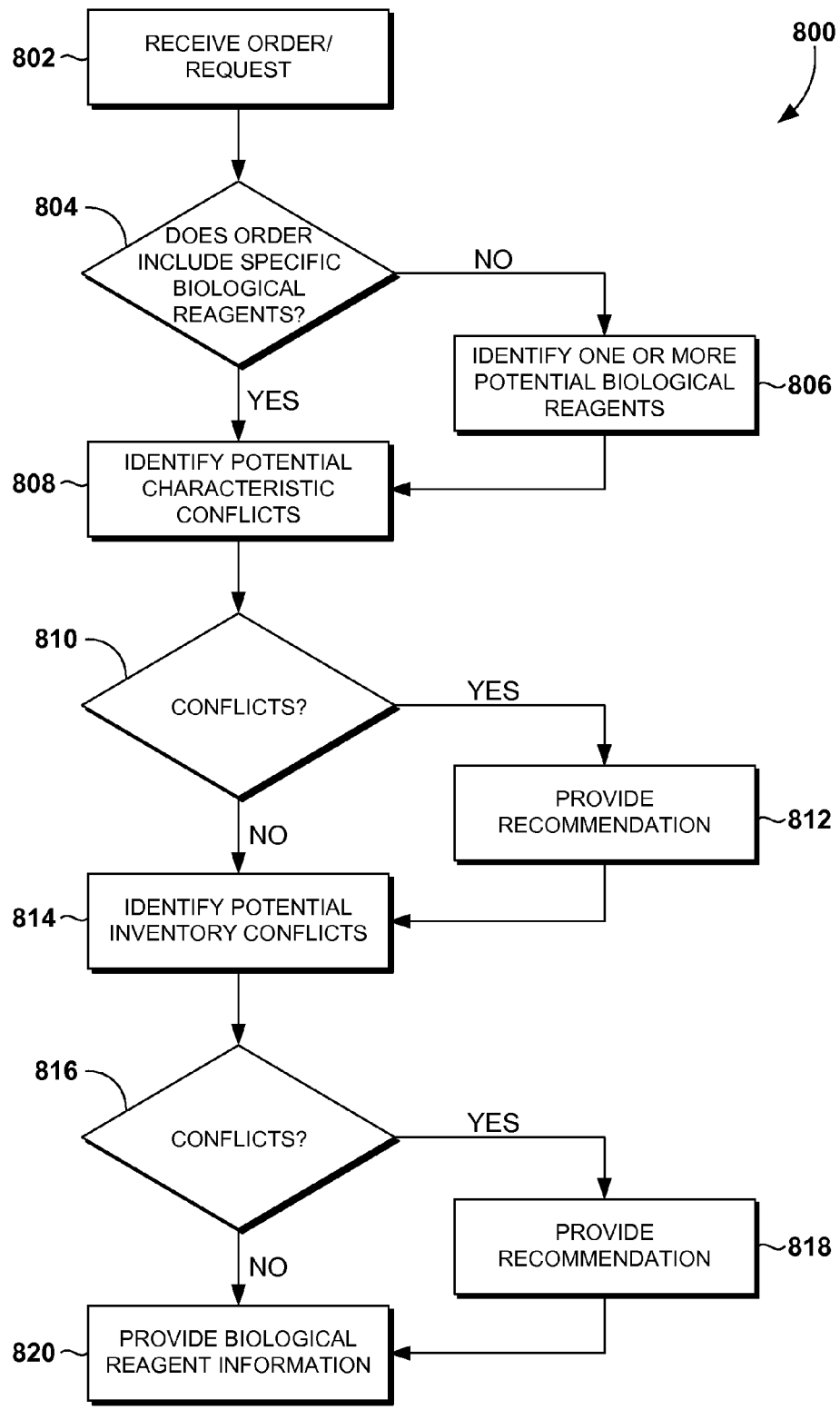
FIG. 8 depicts a block diagram illustrating a method for providing recommended biological reagents in response to a request in accordance with embodiments of the present invention.

Turning to FIG. 8 that depicts a block diagram illustrating a method 800 for providing recommended biological reagents in response to a request in accordance with embodiments of the present invention. At a step 802 an order is received. As used herein, an order includes a biological reagent order, a request, and a request for a biological reagent. As previously discussed, the receiving of a request includes receiving a request by way of a network connection from a healthcare provider. The request may also be received by having the request entered locally. Further, receiving of a request includes receiving a nondigital order, such as a patient's physical record or a written order, which is then input to a computing device for use by a biological reagent catalog.

At a step 804 a determination is made to identify if the received order includes specific biological reagents. In an exemplary embodiment, as previously discussed, a biological reagent order includes a suspected biological condition, but does not include specified biological reagents. In an additional exemplary embodiment, the received order may include specific biological reagents. However, it is contemplated that the order may include an identifier of a specified biological reagent manufactured by a particular entity, such as a trade name FISH probe. In this example, the biological reagent catalog may convert the trade name, based on information accessible locally or from a remote data store, to a functional identifier, such as that provided by the CBO discussed previously. At step 804, when the order does not include a specified biological reagent, the method 800 progresses to a step 806.

At the step 806, one or more biological reagents are identified that are capable of fulfilling the received order. As previously discussed, the order may include a suspected biological condition, such as a form of leukemia, a biological reagent catalog may rely on historical information to identify biological reagents that have been used previously for a similar suspected biological condition. Additionally, it is contemplated that the biological reagent catalog accesses a data store, either locally or remotely, that includes a data structure that is referenced to identify various biological reagents that are useable to fulfill an order including a suspected biological reagent. An additional exemplary embodiment includes querying a user, such as a laboratory technician or a healthcare provider, to input one or more biological reagents capable of fulfilling the order. Regardless of the method employed to identify a potential biological reagent, the potential biological reagent may then be evaluated for identifiable conflicts at a step 808.

In the alternative, at step 804 when the received order is determined to include a specific biological reagent, the method 800 proceeds directly to the step 808 to identify potential characteristic conflicts. As previously discussed, a characteristic conflict exists when one or more characteristics of specified or proposed biological reagents would result in ambiguous or unreliable diagnostic results when used in a testing environment. For example, if two specified biological reagents fluoresce a common color, then a characteristic conflict may exist as an evaluation of the biological reagents after being applied to biological matter would be difficult to differentiate between the similarly colored biological reagents. A characteristic conflict is identified, in an exemplary embodiment, through the evaluation of characteristic information of each biological reagent potentially included with a common order. If characteristics within the characteristic data are similar, a characteristic conflict is identified. Additionally, in another exemplary embodiment, a characteristic conflict is identified when one or more biological reagents included in an order have been previously identified as having a characteristic conflict in either a local or remotely accessible data store containing a database of characteristic conflicts between potential biological reagents. Similarly, it is contemplated that such a database as with all other data stores discussed herein may be updated automatically or manually either by a network connection or other methods.

At a step 810, a determination is made if a characteristic conflict was previously identified, then the method 800 proceeds to a step 812. Alternatively, if a characteristic conflict was not identified, then the method 800 proceeds to a step 814.

At the step 812, the biological reagent catalog provides a recommendation to cure one or more identified characteristic conflicts. For example, the biological reagent catalog may identify one or more individual or combinations of biological reagents that are either known to be comparable or are identified as being comparable to the one or more biological reagents associated with the characteristic conflict. In this example, the recommendation may be based from a database maintained either locally or remotely that identifies one or more alternatives for a biological reagent. Once the alternatives have been identified, the biological reagent catalog may reduce the alternatives to those that would also avoid a similar or additional characteristic conflict. In an additional exemplary embodiment, historical information may provide an indication of one or more alternative biological reagents previously relied upon. The historical data, as previously discussed, may be historical data of a large pool of sources, a particular grouping of sources, or a particular source. Further yet, it is contemplated that an exemplary embodiment identifies, from characteristic data of biological reagents, one or more alternative biological reagents. For example, a region of interest or other indication of an intended probe location of a conflicted biological reagent may be identified and compared to other biological reagents to determine an alternative biological reagent that shares at least a portion of a common region of interest.

In yet an additional exemplary embodiment, the recommendation at step 812 is merely an open dialog in which a user or other entity may provide a manual entry of a substitute biological reagent once a conflict has been identified. It is understood that a similar process may be implemented at any point a substitute biological reagent is required for recommendation purposes.

In the alternative, if no characteristic conflicts were identified at a step 808, the method 800 proceeds to the step 814. The step 814 includes identifying an inventory conflict. For example, once one or more recommended, potential, and/or specified biological reagents are included with an order, they are evaluated to ensure an inventory conflict is not present. As previously discussed, an inventory conflict includes inventory information exceeding, meeting, and/or falling below a predetermined threshold. An example includes determining an expiration date of a biological reagent is at least equal to or later than the current date or scheduled date for the completion of the order. Other examples include identifying the quantity of the biological reagent available. If the quantity is less than a predefined threshold, an inventory conflict may exist that would not prevent the particular biological reagent from being utilized, but it would result in a notification being provided. An additional inventory conflict may include evaluating quality control information to identify when a particular biological reagent is associated with quality control metrics (or statistics) outside of acceptable limits. For example, when a standard deviation of positive or negative results exceeds a predetermined amount, an inventory conflict (which may or may not disqualify the particular biological reagent) may be identified.

As with all conflicts, a notification may be presented to a user or in conjunction with fulfillment with an order. The notification may include a warning as to the potential conflict, such as that previously discussed with respect to FIG. 7. A data structure may include default actions depending on the type of conflict. For example, the default for an inventory conflict when the quantity available is zero may have a default option of providing an alternative biological reagent. To the contrary, an inventory conflict in which the quantity available is at or below a predefined threshold, the default may be to provide a notification as to the conflict, but maintain the current biological reagent in the order (or provide alternative biological reagents as an option). The data store including the default options may be provided by a remote source, or it may be stored locally. As previously discussed, any combination of local and remote storage and update may be implemented to achieve the functionality described herein. Similar to a threshold analysis discussed hereinabove, an inventory control, in an exemplary embodiment, results in an inventory conflict. An inventory control is a predefined threshold at which a conflict is identified. For example, an inventory control may be set so that when the quantity of a biological reagent falls below a predefined threshold, then an inventory conflict is identified.

The method 800 includes a step 816 at which an inventory conflict is determined to exist or not. If an inventory conflict does exist, a step 818 provides a recommendation. Similar to the options previously discussed with respect to the step 812 for providing a recommendation, the step 818 may implement at least those methods to provide a recommendation. For example, historical information may be utilized to identify one or more alternative biological reagents. Similarly, characteristic data of the one or more biological reagents may be evaluated to identify alternative biological reagents that have common characteristic data that may allow a similar result to be attained.

If an inventory conflict does not exist, at a step 820 a recommendation of biological reagents is provided. In an exemplary embodiment, the recommendation includes one or more biological reagents able to fulfill the order received at the step 802. The recommendation may be provided as a visual output to a GUI, as an entry into an electronic medical record, or as an order that is passed on to an order-fulfillment mechanism or device. In yet an additional exemplary embodiment, the provided biological reagent information may include one or more options from which a user may select. For example a first option includes a first set of biological reagents while a second option includes at least one alternative (if not more) biological reagents from the first option.

It is contemplated the method 800 may be implemented in any order and that the particular illustration provided in FIG. 8 is merely one of the many possible orders in which the method may be implemented. For example, it is contemplated that following the providing of a recommendation (e.g., steps 812 and 818) that the method 800 returns to identifying initial conflicts (e.g., characteristic, inventory). As such, a later provided recommendation will therefore be free of an earlier evaluated conflict type. However, it is also contemplated that the later provided recommendations may, in an exemplary embodiment, be drawn from a pool of candidates that are free from previously evaluated conflicts. Further, it is contemplated that the present invention may forbear one or more of the steps discussed above while still achieving functionality of embodiments of the present invention.

Not depicted, but still contemplated, data stores may be updated throughout the process. For example, inventory characteristic information and inventory controls may be updated based on each biological reagent order and/or recommendation. Additionally, it is contemplated that the biological reagent catalog has access to results of the biological reagents in order to verify usage of biological reagents and to maintain and/or update quality control information.

Figure 9:
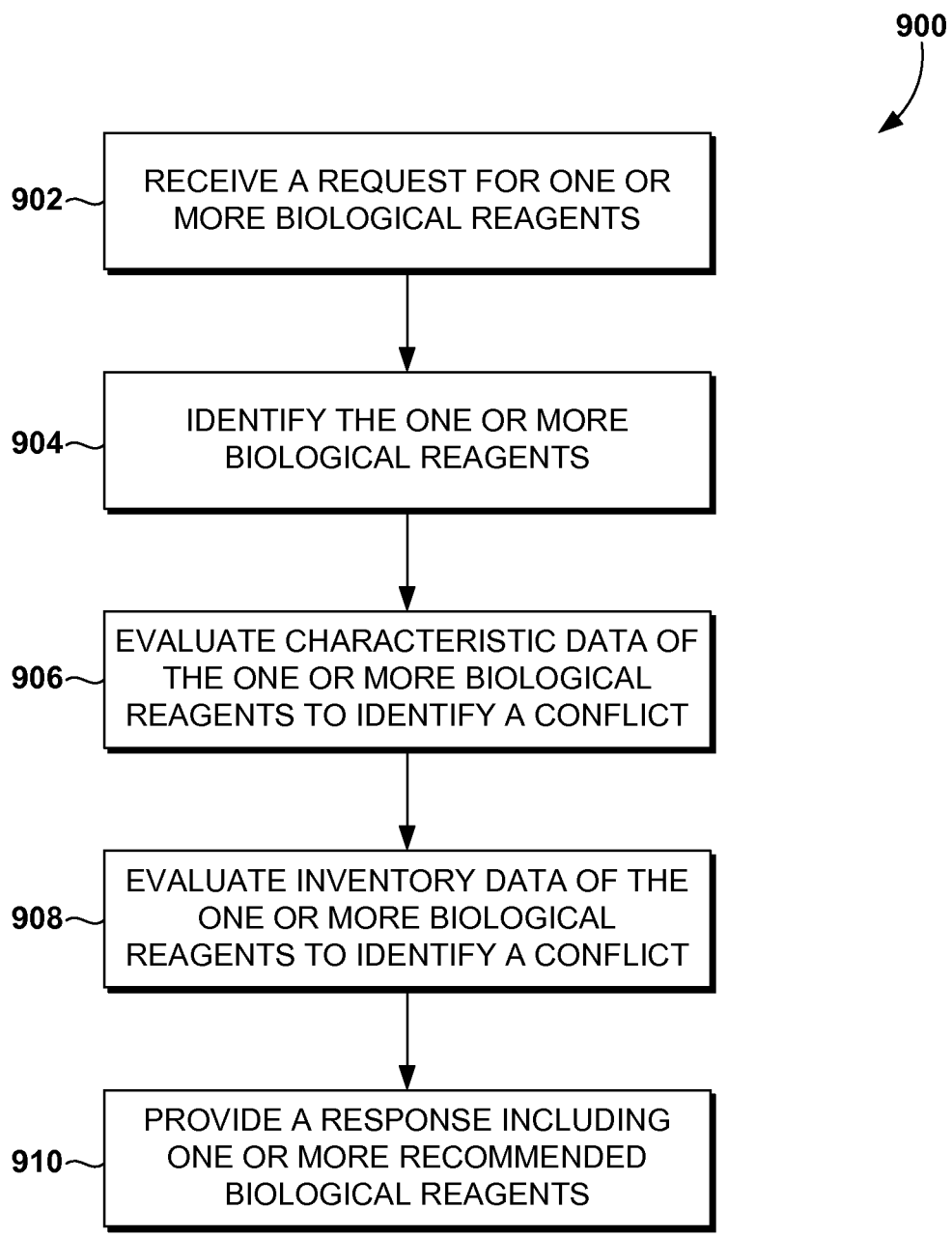
FIG. 9 depicts a method for providing recommended biological reagents in response to a biological reagent order in accordance with embodiments of the present invention.

Turning to FIG. 9 that depicts a method 900 for providing recommended biological reagents in response to a biological reagent order in accordance with embodiments of the present invention. At a step 902 a request for one or more biological reagents is received. Depending on the format in which the biological reagents are received, the one or more biological reagents are identified at a step 904. Identifying of the one or more biological reagents may include associating a functional nomenclature with the biological reagents. The functional nomenclature, as previously discussed allows for a universal naming convention to be used that identifies functionality for each of the biological reagents. In an additional exemplary embodiment, the identification of the one or more biological reagents includes recommending one or more biological reagents based on the request, which may only include a suspected biological condition or the like. Therefore, based on historical data, or other data sources previously discussed, one or more biological reagents are identified for the request received at the step 902.

At a step 906, characteristic data of the one or more biological reagents are evaluated to identify a conflict. As discussed with respect to FIG. 8, a characteristic conflict may be identified based on a variety of criteria including, but not limited to, historical data, predefined conflict sets (known conflicts), or a comparison of the characteristic data.

At a step 908 inventory data of the one or more biological reagents is evaluated to identify a conflict. Similar to the previous discussion with respect to FIG. 8, the evaluation of inventory data may include identifying expired, low quantity, or even quality control concerns among other potential conflicts.

At a step 910, a response is provided that includes one or more recommended biological reagents. The recommended biological reagents are derived from the evaluation of characteristic data, inventory data, and the like in view of the original request. As a result, the recommended biological reagents included with the response are able to fulfill the original intent of the request received at the step 902. In an exemplary embodiment, the recommended biological reagents provided in the response are the same biological reagents originally provided with the request when a conflict is not identified.

Figure 10:
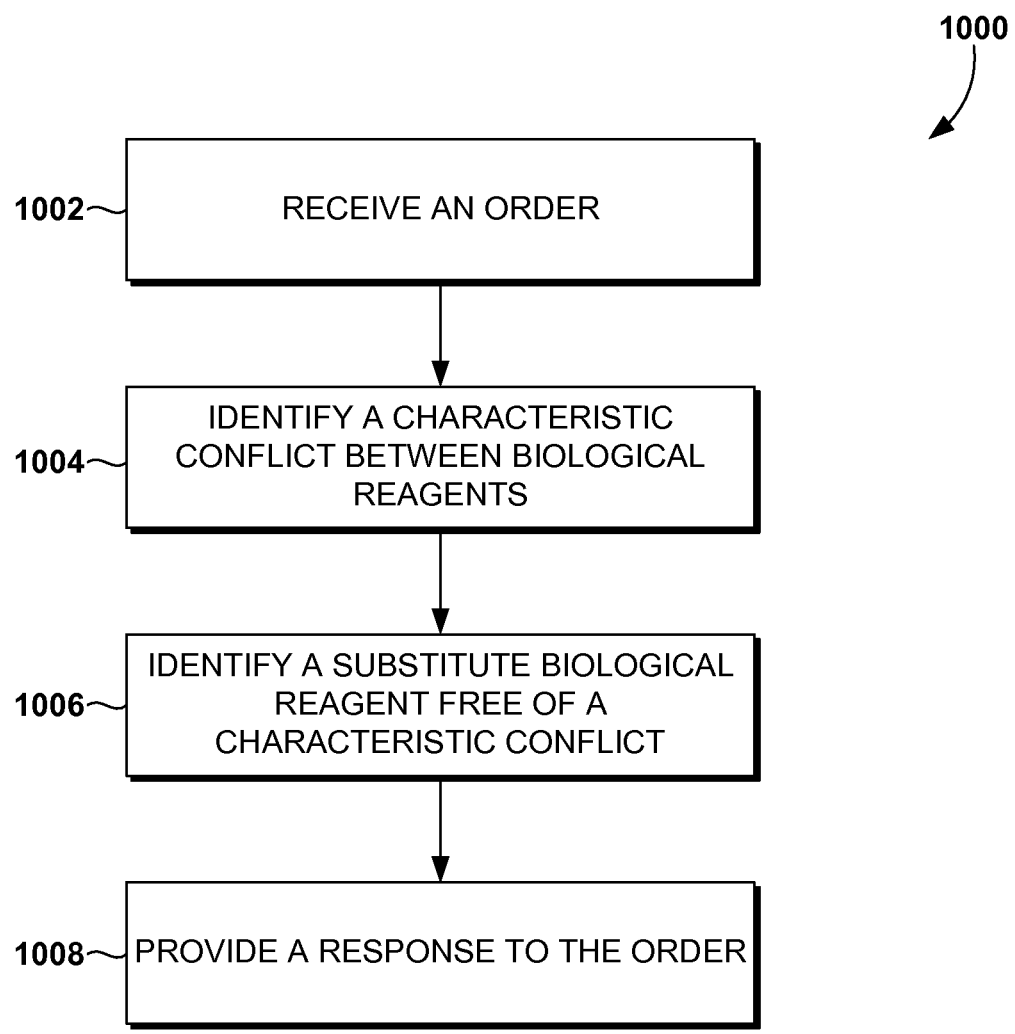
FIG. 10 depicts a method for providing recommended biological reagents in response to a biological reagent order in accordance with an exemplary embodiment of the present invention.

Turning to FIG. 10 that illustrates a method 1000 for providing recommended biological reagents in response to a biological reagent order in accordance with an exemplary embodiment of the present invention. At a step 1002 an order is received. In an exemplary embodiment, the order includes one or more specified biological reagents or at least information, such as a suspected biological condition, from which a biological reagent may be identified.

Characteristic data associated with the one or more biological reagents of the order is evaluated to identify a conflict between the one or more biological reagents as indicated at a step 1004. When a characteristic conflict is identified, a substitute biological reagent is identified at a step 1006. The substitute biological reagent is a biological reagent that is functional to achieve a similar result as at least one of the conflicted biological reagents; however, the substitute biological reagent is free from a characteristic conflict. At a step 1008, a response to the order is provided. The response includes one or more biological reagents comprised of the originally identified biological reagents and/or substitute biological reagents so long as the biological reagents included with the response are free from characteristic conflict and achieve the underlying intent of the original order.

Figure 11:
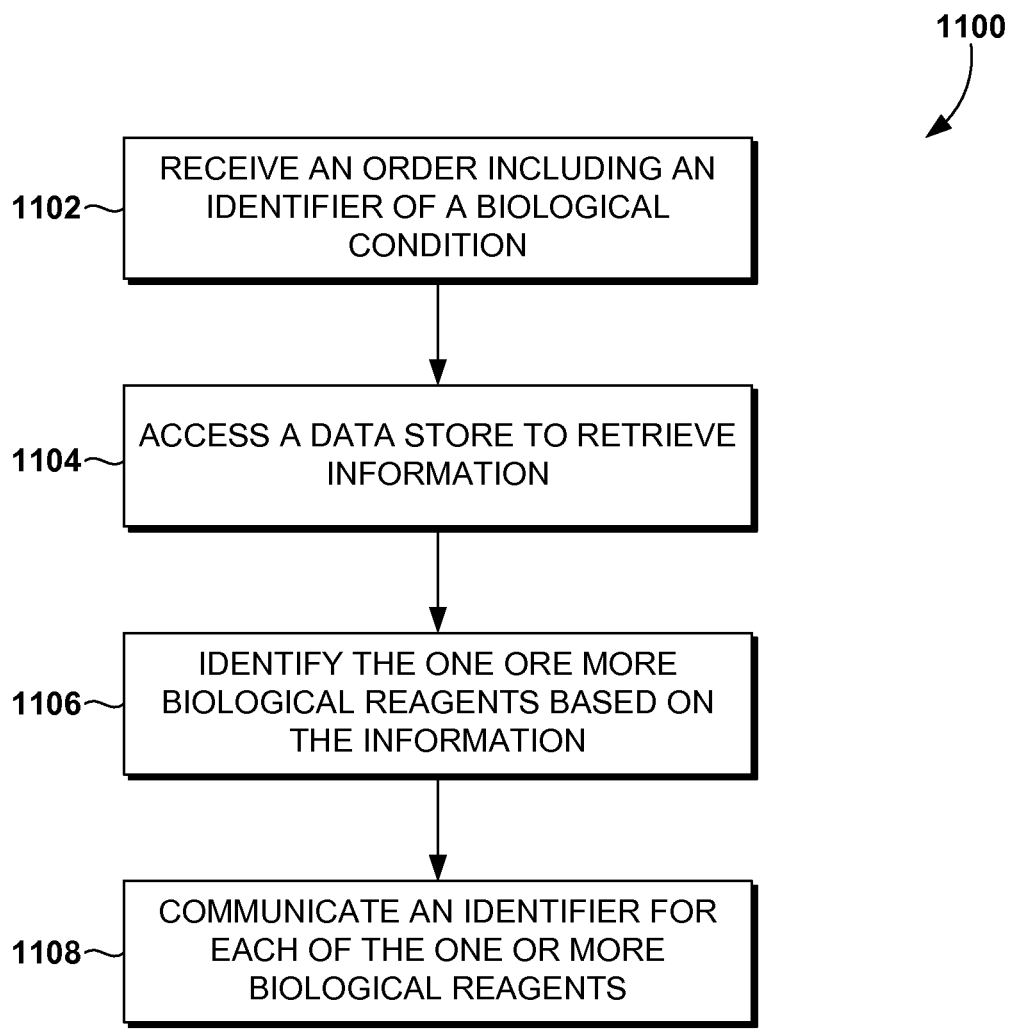
FIG. 11 depicts a method for identifying one or more biological reagents associated with a biological reagent order in accordance with an embodiment of the present invention.

Turning to FIG. 11, that depicts a method 1100 for identifying one or more biological reagents associated with a biological reagent order in accordance with an embodiment of the present invention. At a step 1102 an order is received including an identifier of a biological condition. The identifier may include a suspected biological condition, a suspected abnormality, or the like that may be examined through the use of biological reagents. The identifier may be in a format specified by a predefined set of rules and/or standards or the identifier may be contextually deciphered to understand an underlying intent.

At a step 1104, a data store is accessed to retrieve information. In an exemplary embodiment, the data store includes historical data that includes information related to those biological reagents previously utilized in association with the identifier of a biological condition. In an additional exemplary embodiment, the data store includes a predefined mapping between identifiers and biological reagents functional for testing a biological condition associated with the identifier.

At a step 1106, one or more biological reagents are identified based on the information. For example, the information may identify various regions of interest that are necessary to identify and the information may also include characteristic data of biological reagents so that an evaluation of the characteristic data identifies those biological reagents that are functional to identify the regions of interest indicated in the information. As a result, biological reagents are identified.

At a step 1108, an identifier of the one or more biological reagents is communicated. In an exemplary embodiment, communication includes providing a visual indication by way of a display device. In an additional exemplary embodiment, communication includes providing an updated order to an order fulfillment system or entity. Further yet, communication includes the concept of a remote server at which the identification of the biological reagent is performed and the resulting identification is communicated to a remote computing device where the order may have originally originated.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more computer storage media having computer-executable instructions embodied thereon, that when executed by a computing system having a processor and memory, cause the computing system to perform a method for providing recommended biological reagents in response to a request, the method comprising:
   receiving, at the computing system, a request for one or more biological reagents, wherein the request is comprised of a suspected biological condition;
   identifying the one or more biological reagents capable of fulfilling the request;
   evaluating, with the computing system, characteristic data of the one or more biological reagents to identify a characteristic conflict with at least one characteristic of the one or more biological reagents;
   evaluating inventory data of the one or more biological reagents to identify an inventory conflict with one or more inventory controls of the one or more biological reagents; and
   providing, in response to the request, a response including one or more recommended biological reagents, wherein the one or more recommended biological reagents are provided based, at least in part, on the evaluation of the characteristic data and the evaluation of the inventory data.

2. The method of claim 1, wherein the request for one or more biological reagents is received from a healthcare provider.

3. The method of claim 1, wherein the one or more recommended biological reagents are Fluorescence In Situ Hybridization (FISH) Probes.

4. The method of claim 1, wherein receiving a request for one or more biological reagents is further comprised of one or more specified biological reagents.

5. The method of claim 4 further comprising accessing a data store to convert each identifier of the one or more specified biological reagents to a functional ontology identifier for each of the one or more specified biological reagents.

6. The method of claim 1, wherein the characteristic data includes one or more characteristics of the one or more biological reagents, a characteristic is an characteristic of a biological reagent that is relied upon during utilization of the biological reagent.

7. The method of claim 1, wherein the evaluation of inventory data includes evaluating at least one of a metric of quantity available, an expiration date, or a quality control statistic.

8. The method of claim 1, wherein a characteristic conflict or an inventory conflict causes an unreliable result from a diagnostic test utilizing the one or more biological reagents.

9. The method of claim 1 further comprising updating the inventory data, wherein the inventory data is updated to reflect a change in quantity of the one or more recommended biological reagents.

10. The method of claim 1 further comprising maintaining, in a data store, historical data associated with the request, wherein the data is comprised of at least one of: an originator of the request, a patient associated with the request, the one or more biological reagents, the one or more recommended biological reagents, characteristic data of the one or more recommended biological reagents, or inventory data of the one or more recommended biological reagents.

11. The method of claim 1 further comprising:
providing access to a catalog entry form;
receiving the characteristic data for the one or more biological reagents;
storing the characteristic data in a data store;
generating functional nomenclature identifiers for the one or more biological reagents utilizing the characteristic data;
mapping the functional nomenclature identifiers to the one or more biological reagents; and
utilizing the functional nomenclature identifiers to identify the one or more biological reagents.

12. A computer-implemented method providing recommended biological reagents in response to a biological reagent order, the method comprising:
receiving, at a computing device having a processor and memory, the order, wherein the order includes a first biological reagent and a second biological reagent;
identifying, with the computing device, a characteristic conflict between the first specified biological reagent and the second biological reagent;
identifying, with the computing device, a third biological reagent as a substitute for the second biological reagent, wherein the first biological reagent and the third biological reagent are free of the characteristic conflict; and
providing a response to the order that identifies at least the first biological reagent and the third biological reagent.

13. The method of claim 12, wherein the order is received by way of at least one of the following: a local network, a local area network, a wide area network, or the Internet.

14. The method of claim 12 further comprising converting a nomenclature of the first and the second biological reagents to a functional nomenclature that is descriptive of one or more characteristics of the respective biological reagent.

15. The method of claim 12, wherein a characteristic conflict results in an unreliable diagnostic result based on the first biological reagent and the second biological reagent.

16. The method of claim 12, wherein identifying the third biological reagent includes evaluating characteristic data of the second biological reagent to identify that the third biological reagent includes similar diagnostic functionality to the second biological reagent.

17. The method of claim 12, wherein identifying the third biological reagent includes evaluating historical data to identify the third biological reagent.

18. The method of claim 12, wherein the third biological reagent includes diagnostic functionality that is similar to the second biological reagent.

19. The method of claim 12 further comprises evaluating inventory data associated with the first biological reagent and the third biological reagent.

20. One or more computer storage media having computer-executable instructions embodied thereon, that when executed by a computing system having a processor and memory, cause the computing system to perform a method for providing one or more biological reagents for a diagnostic test, the method comprising:
receiving an order for one or more biological reagents to perform a diagnostic test functional to identify a biological condition, wherein the order includes an identifier of the biological condition;
accessing, with the computing system, a data store to retrieve information, wherein the information includes characteristic data, inventory data, and historical data of one or more biological reagents;
identifying, with the computing system, the one or more biological reagents based on the information, wherein a conflict threshold is exceeded by the one or more biological reagents as determined from the information; and
communicating an identifier for each of the one or more biological reagents.

* * * * *